United States Patent [19]
Cockrem

[11] Patent Number: 5,522,995
[45] Date of Patent: Jun. 4, 1996

[54] PROCESS FOR RECOVERING ORGANIC ACIDS FROM AQUEOUS SALT SOLUTIONS

[76] Inventor: Michael C. M. Cockrem, 224 Westmorland Blvd., Madison, Wis. 53705

[21] Appl. No.: 395,621

[22] Filed: Feb. 28, 1995

[51] Int. Cl.$^6$ .................................................. B01D 61/12
[52] U.S. Cl. ......................... 210/637; 210/654; 210/259
[58] Field of Search .................................. 210/634, 650, 210/651, 652, 653, 654, 259, 637

[56] References Cited

U.S. PATENT DOCUMENTS

| | | | |
|---|---|---|---|
| 4,480,034 | 10/1984 | Hsieh | 435/136 |
| 5,057,197 | 10/1991 | Perry et al. | 240/182.4 |
| 5,266,342 | 11/1993 | Spence et al. | 426/427 X |
| 5,338,575 | 8/1994 | Nasr et al. | 426/427 |

Primary Examiner—Frank Spear
Attorney, Agent, or Firm—Andrus, Sceales, Starke & Sawall

[57] ABSTRACT

A crude aqueous mixture of basic salts of an organic acid, free organic acid, and impurities is mixed with carbon dioxide under pressure and applied to a membrane such as a reverse osmosis or other membrane with small pores while holding the mixture under pressure with well mixed carbon dioxide, such that the free organic acid preferentially permeates the membrane while the impurities and salts of the organic,acid are preferentially but not necessarily completely retained. In The preferred form of the invention a back pressure is maintained on the permeate side of the membrane that is a significant pressure but less than the pressure applied to the feed side. This allows higher levels of acidification to be achieved. This is necessary as many membranes are permeable to $CO_2$ choices of membrane permeate side pressure, retentate side pressure, and permeate counter flow rate can be used to effect different levels of either purification or concentration or both.

16 Claims, 1 Drawing Sheet

PROCESS FOR RECOVERING ORGANIC ACIDS FROM AQUEOUS SALT SOLUTIONS

BACKGROUND OF THE INVENTION

Various membrane systems can be used to separate chemicals of different species. Often they are used to remove water from a dilute solution to produce a concentrated product. Sometimes other species are removed with the water.

Reverse Osmosis (RO) is a crossflow membrane technology that was developed more than 35 years ago. A typical membrane is synthetic polymer coated onto a backing material so as to create pores that are only a few Angstoms in diameter. Purified water passes through the membrane and other contaminants are rejected or retained by the membrane. Membrane materials include cellulose acetate (CA), polyamide (PA), and sulfonated polysulfone (SPS).

The typical RO system feeds impure water at high pressure to the one side of the membrane and removes purified water from the other side of the membrane at low pressure, near atmospheric. The greater the driving force, the better the flow of water and the greater the separation effectiveness of salts such as sodium chloride from the water. The high pressure side product is thus depleted of water, and if left containing a more concentrated solution of the salts. This is called the retentate. The low pressure side contains the purified water and is called the permeate.

As the salt is rejected by the RO membrane, the osmotic pressure on the retentate side increases. This means that the water is increasingly retained on the retentate side by attraction to the salt species. Thus it is often necessary and desirable to use high pressures on the retentate side and low pressures on the permeate side to allow greater concentration of the retentate. In addition, the greater the transmembrane pressure, the higher the flux.

Often RO membranes are designed to try to reject all salts and organic species except water. A typical water purification system may run at 400–600 psig on the retentate side and 5–10 psig on the permeate side. For example, hollow fibre membrane bundles use small fibres to withstand the high retentate side pressure and an economical plastic housing on the permeate side to collect the purified water.

Nanofiltration (NF), ultra-osmosis (UO), and loose reverse osmosis (loose RO) are all terms used to describe membranes that permeate some low molecular weight materials or salts while retaining others. The present description and specification will use NF to represent all of these processes. They are very similiar to RO. Some common NF membranes are used to permeate water and sodium ions and chloride ions, while rejecting (and thus retaining) calcium salts and also retaining sugars such as lactose.

Organic acid recovery from salts is necessary for purification of fermentation broths, neutralized wood processing wastes for example such as those containing sodium acetate, and memory other organic acid streams. Organic acids are present in streams such as fermentation broths, pulping waste streams, citrus processing waste streams. This invention applies to streams containing salts of organic acids that are in the pH range 3 to 8.

Acids by fermentation can be produced by the continuous or batch fermentation of sugars or other biomass streams such as hydrolysed starch, sulfite waste liquor, or cheese whey. For example lactic acid can be produced by the continuous or batch fermentation of sugars or other biomass streams such as hydrolysed starch, sulfite waste liquor, or cheese whey. For a rapid and economic fermentation, the pH of the broth is usually maintained in the rage of 4.5 to 7.5 by either (a) continuously removing lactic acid such as by extraction, or membranes, or ion exchange, or electrodialysis, or (b) continuously adding a base such as aqueous ammonia, calcium carbonate, calcium hydroxide, or sodium hydroxide, or (c) starting the fermentation with a growth medium with substantial buffering capacity, such as a calcium carbonate slurry.

In case (a) the fermentation is integrated with the first step of the product recovery process. At a pH of 5 to 7 at 30°–50° C., the lactic acid is present mainly as lactate salts rather than free acid.

In cases (b) and (c) and in some variants of case (a) above, the fermentation product is a crude aqueous broth at pH 4 to 8 containing 1 to 20% weight lactate salts, together with impurities such as medium components, neutralizing agent impurities, biomass, and salts of other acids. In each case, the fermentation broth may or may not have the fermentation micoorganisms or enzyme slurry removed by methods such as centrifugation, membranes processes, coagulation, or other methods, and this removal may take place during or after the production of the crude fermentation broth.

Other typical organic acids and microorganisms for their production that are disclosed by Atkinson and Mavituna (Biological Engineering and Biotechnology Handbook p 421 (1983)) Nature Press, are as follows:

| Acid | One example of a microorganism that can produce this acid |
|---|---|
| Acetic acid | Acetobacter acetii |
| L-allo-isocitric acid | Penicillium purpurogenum |
| beta-Arabo-ascorbic acid | Penicillium notatum |
| Citric acid | Aspergillus niger |
|  | Candida lipolytica |
| Fumaric acid | Rhizopus delemar |
| Gluconic acid | Aspergillus niger |
| L-isocitric acid | Candida brumptii |
| Itaconic acid | Aspergillus terreus |
| 2-ketoglyconic acid | Pseudomonas fluorescens |
| 5-ketogluconic acid | Gluconobacter suboxydans |
| alpha-ketoglutaric acid | Candida hydrocarbofumarica |
| Kojic acid | Aspergillus oryzae |
| Lactic acid | Lactobacillus delbruckeii |
| Malic acid | Lactobacillus brevis |
| Propionic acid | Propionibacterium shermanii |
| Pyruvic acid | Pseudomonas aeruginosa |
| Succinic acid | Bacterium succinicum |
| Tartartic acid | Gluconobacter suboxydans |

This invention pertains to salts of organic acids including salts of aliphatic monocarboxylic acids containing 1 to 5 carbon atoms, e.g. formic acid, acetic acid, propionic acid, butyric acid, and pentanoic acid; salts of aliphatic alpha hydroxy monocarboxylic acids containing 2 to 4 carbon atoms, e.g. hydroxyacetic acid, lactic acid and alpha hydroxy-butyric acid; salts of aliphatic beta hydroxy monocarboxylic acids containing 3 or 4 carbon atoms, e.g. 1-hydroxy-3-propionic acid and beta hydroxy butytric acid; salts of olefinic monocarboxylic acids containing 3 to 4 carbon atoms such as acrylic acid and methacrlyic acid; and salts of dicarboxylic acids containing 3 to 4 carbon atoms such as succinic acid.

Some of the problems of organic acid recovery from salts include:

(a) Purity — Often a high purity product is required. Many processes require many steps to achive this purity (b) Thermal processing — Any process that requires thermal processing as part of the purification sequence will likely generate undesirable reaction products and/or precipitates.

(c) Base recovery — Many processes require addition directly or indirectly of a strong inorganic acid such as hydrochloric acid or sulfuric acid to release the organic acid from its salt. These processes generate a new dilute or concentrated solution containing the salt of the new inorganic acid. For example calcium lactate is contacted with sulfuric acid to release lactic acid and to produce calcium sulfate which precipitates. The calcium sulfate must then be removed and dealt with. Calcium hydroxide or calcium carbonate is not readily recovered for reuse from this process.

Electrodialysis can separate the organic acid salt into free acid and regenerated base which can be re-used for fermentation or other pH control needs. These processes require elaborate membrane systems and typically have significant electricity costs.

(d) Cost — a simple, low temperature, solids-free process is likley to give the lowest cost.

(e) Complexity — a simple process that leads directly to a high purity product is desirable.

Another important separation process involves weak organic base recovery. This is the inverse of the case of organic acid recovery. Instead of recovering the organic acid from its salt solution, recover the organic base from its salt solution is recovered. For example, consider the case of the recovery of amines used to scrub acid vapors. Here an amine such as ethylamine may be contacted with an acid such as HCL to scrub the acid from vapor. The resultant solution of the chloride salt of the amine must then be recovered and regenerated for re-use.

Still another important area is amino acid recovery. Amino acids such as lysine may be produced by fermentation. In these processes, the pH is often controlled to aid performance of the fermenting micro-organisms. Amino acids are called amphoteric, in that they have both acidic and basic groups. All amino acids have a common formula:

$$HOOC-CR_1R_2-NH_2$$

where $R_1$ and $R_2$ are simple or complex side groups. If the pH of the broth is controlled with ammonia, then the resultant species in solution will be

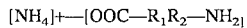

$$[NH_4]+-[OOC-R_1R_2-NH_2]$$

Separation of the free amino acid from the salt is often done by various means including ion exchange. In the current invention, there is show and described a new way to recover amino acids.

Shimshick (1981) U.S. Pat. No. 4,250,331 reports a supercritical extraction-acidification process for recovering carboxylic acids from dilute aqueous solutions of alkali metal salts of such carboxylic acids. Feed solutions are mixed with 10 to 1000% of a supercritical solution comprising at least 10 mole carbon dioxide. The salt reacts with the carbon dioxide to form the carboxylic acid which dissolves in the supercrical fluid phase. The aqueous and supercritical phases are then separated. The pressure of the supercritical phase is then lowered so that an acid phase is formed separate from the supercritical phase, whereby the acid is recovered. This differs extensively from the current invention. The current invention does not use extraction, does not require use of supercritical conditions, but only requires use a membrane system.

Yates (1981) U.S. Pat. No. 4,282,323 reports a sub-critical extraction acidification process, very similiar to that of Shimshick. The key difference is that the Shimshick patent uses supercritical carbon dioxide as the extracting solvent, whereas the Yates patent uses a polar organic extracting with carbon dioxide under pressure.

Donohue et al (1989) report using a cellulose acetate membrane to separate carbon dioxide — methane gas mixtures. They found that the permeability of carbon dioxide through the membrane increased dramatically with pressure. They believed that this was due to plasticization of the cellulose acetate by the carbon dioxide.

Awadalla et al (1994) used membranes to remove ammonium and other ionized species from mining waste water. They report that reverse osmosis membranes (the exact type was not specified) were found to provide good rejection of ammonium ion (>99%) while poor rejection of free ammonia (10–30%). Here we see that a membrane system can be used to achieve a pH dependent separation.

Some membranes exhibit excellent rejection of free acid form of organic acids, and others exhibit poor rejection. Examples are

TABLE 1

Examples of some membranes exhibiting excellent rejection (% rej) of free acids

| Membrane | Solute | Feed conc wt % | % Rej |
|---|---|---|---|
| Polyamide (FT-30) | acetic acid | 0.07 | 92 |
| Polyamide (FT-30) | butyric acid | 0.09 | 95 |
| TFC (PCI ZF99) | lactic acid | 1.0 | 90–95% |

TABLE 2

Examples of some membranes exhibiting poor rejection (% rej) of free acids

| Membrane | Solute | Feed conc wt % | % Rej |
|---|---|---|---|
| Cellulose acetate | acetic acid | 1.0 | 7 |
| Cellulose acetate (CA-97) | lactic acid | | 20–40% |

TABLE 3

Examples of membrane exhibiting poor rejection (% rej) of free base but good rejection of ionized base Methylamine removal

| acidic solution | 98% removal |
|---|---|
| basic solution | 50% removal |

NS-100 membrane microporous polysulfone coated with polyethylenimine which is crosslinked with m-tolylene-2,4-diisocyante.

TABLE 4

Literature Data for acetic
acid/acetate and a NS-100 membrane.

| % Dissociation of acetate | pH | % Removal of acetate |
|---|---|---|
| .99 | 6.75 | 97% |
| .80 | 5.36 | 80% |
| .40 | 4.58 | 50% |
| .20 | 4.15 | 42% |
| .01 | 2.76 | 30% |

TABLE 5

Literature Data for separation of lactic acid
from lactate using an HC-50 polyamide on
polysulfone thin film composite membrane.
1% w/w lactic acid solution

| pH | % dissociation of lactate | % rejection of lactate |
|---|---|---|
| 6.00 | 99.9% | |
| 4.93 | 98.6% | 80% |
| 4.43 | 95.8% | 72% |
| 3.93 | 87.9% | 60% |
| 3.45 | 70.6% | 43% |
| 2.88 | 39.2% | 32% |
| 2.00 | 7.8% | |

TABLE 6

Literature Data for separation of acetic acid from
water and for separation of sodium acetate from
water using a DuPont Hollow Fibre B-9 permeator,
at 500–680 ppm feed concentration

| pH | % dissociation of acetate | % rejection of acetate |
|---|---|---|
| 8.1 | 99.95% | 98% |
| 3.7 | 8.06% | 40% |

SUMMARY OF THE INVENTION

This invention relates to a process for recovery of purified acid from crude or partially purified broth containing acid and basic salt of acid, comprising the following:

1. acidifying a crude or partially purified broth with pressurized carbon dioxide;

2. separating the acid from the broth using a reverse osmosis membrane or other suitable membrane which rejects salts of the organic acid but permeates the acid form, this step is done with $CO_2$ present and optionally with some backpressure maintained on the permeate side to prevent $CO_2$ gas release on the permeate side;

3. collecting the permeate and retentate — and optionally letting the pressure down so that the $CO_2$ gas is released.

The retentate stream may be recycled for reuse as a neutralizing agent. The permeate stream may be used as is, or concentrated and purified further.

The invention pertains to the purification of any crude broth containing a mixture of salts of organic acid and free acid itself, regardless of the exact sequence of steps used to prepare the crude broth. The invention can also be extended to the case of organic base recovery and to the case of amino acid recovery.

BRIEF DESCRIPTION OF THE DRAWINGS

The drawings illustrate the best mode presently contemplated of carrying out the invention.

In the drawings.

DETAILED DESCRIPTION OF THE PREFERRED EMBODIMENT

Figure 1:
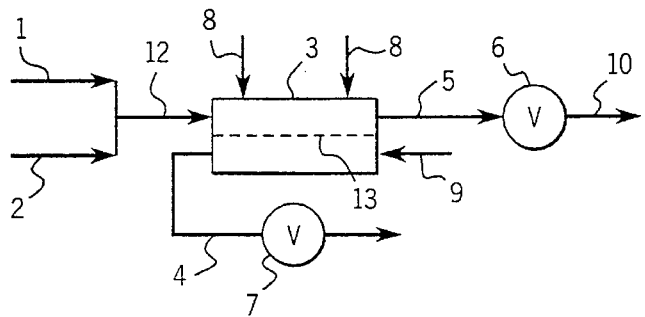
FIG. 1 is a schematic diagram of a single stage process for recovering organic acids from an aqueous solution in accordance with the present invention.

One form of the invention is shown in FIG. 1. In FIG. 1 a feed line 1 containing an aqueous solution of organic acid and salts thereof is mixed with carbon dioxide in line 2 under pressure and fed via line 12 to membrane system 3. The permeate, material which passes through membrane 13 in system 3, is withdrawn via line 4. The retentate exits from the membrane system 3 via line 5 with significant backpressure, controlled by valve 6. In one form of the invention, where the membrane 13 has high carbon dioxide permeability, the permeate in line 4 is retained under backpressure using backpressure valve 7. In one form of the invention, makeup water can be added via line 8 at one or several points along the length of the retentate side of the membrane system 3. In another form of the invention, makeup water or other solvent may be added to the permeate side via line 9 to help carry off permeated product in permeate line 4.

The invention is useful in that it allows recovery of acid from basic salt solution without the addition of strong mineral acid. The retentate in line 10 can be recycled to provide pH control, such as in a fermenter. Also, as well as acidification, the membrane system provides significant purification. In addition, the process utilizes carbon dioxide which is widely available and non-toxic.

The invention is novel in that no systems combining acidification by use of carbon dioxide with the use of special acidity dependent properties of membranes have previously been reported or suggested.

The invention is unobvious in that most membrane systems in use do permeate carbon dioxide and also do not allow significant back pressure on the permeate side. Thus most current commercial equipment cannot be used for this process. Modified or redesigned equipment and/or operating procedures are required. Furthermore the extent of acidification using carbon dioxide is usually thought of as being low. The use of a membrane system allows taking advantage of these acidification properties.

The present specification first presents predictions of the extent of acidification of the salt of some organic acids by using carbon dioxide under various conditions for various organic acid salt solutions. Then the specification presents membrane performance data. As a result, these two previously un-combined technologies can be usefully combined to achieve separation, despite the limited extent of acidification achieved by the weak carbonic acid formed.

One potential problem stems from the permeability of many membranes to carbon dioxide. This problem is overcome in one form of the invention by the use of backpressure on the permeate side of the membrane system. As most membrane systems are designed to run without any significant backpressure of the permeate side, modified equipment and operating procedures are required.

Another potential problem is the increasing basicity of the retentate solution as the acidic species is preferentially removed while leaving behind a buffered bicarbonate solution of the basic salt. Staging calculations indicate that despite this apparent reason why the technology should not work, it indeed will. This is due to the continuous flow feed side stream along the length of a membrane system.

The extent of acidification by carbon dioxide is checked at the "weak" end of the extractor. A small but sufficient level of acidification occurs. This allows for continued removal of free acid species.

Calculations show that careful balancing of feed and permeate pressures and makeup water addition is required to achieve good separation in a reasonable amount of membrane area without excessive dilution of any of the streams.

The acidification process

Here we calculate the fraction of free acid present in various mixtures under different $CO_2$ pressures.

Using equilibrium equations, conservation of charge, and assuming a Henry's Law approximation, we can show that for monovalent salts of organic acids (neglecting non-idealities of the system).

$$h^3+(s+Ka+q)h^2-(K1*n+Ka*a)h-Ka*K1*n=0$$

where
- h = concentration of hydrogen ions
- s = initial concentration of monovalent salt of organic acid
- Ka = acid dissociation constant
- K1 = bicarbonate — aqueous $CO_2$ dissociation constat
- q = initial concentration of monovalent salt of bicarbonte
- n = $HpCO_2$ = cocnentration of dissolved $CO_2$
- H = Henry's Law Constant for $CO_2$ dissolution in solution
- $pCO_2$ = pressure of gaseous carbon dioxide on the system We solve for h, then calculate the system pH $$pH=-log10(h)$$

Next we determine the fraction of the total organic acid species present as free acid $$\frac{a\text{-free}}{a\text{-total}} = 1 - \frac{Ka}{Ka+h}$$

And finally the wt % of free acid in the solution $$\text{wt \% free acid} = \text{wt \% total acid species} * \frac{a\text{-free}}{a\text{-total}}$$

For example, we consider the case of a 10% sodium acetate solution. At 50 atm pressure of carbon dioxide, we find that 0.20 fraction of the sodium acetate species present are converted to acetic acid. This corresponds to the rich end of our membrane system. The total free acid concentration is thus 0.20 fraction × 10% total acid = 2% w/w free acid concentration. This is the free acid that can permeate the acid permeable membrane.

Consider then for example the weak end of the membrane system. Here 90% of the total acid species have permeated the membrane. The sodium bicarbonate has been largely rejected by the membrane. Thus we find that, in the abscence of $CO_2$ the solution remaining solution is 9% sodium bicarbonate and 1% sodium acetate. These calculations show that of the 1% sodium acetate left, again 0.20 fraction is converted to free acetic acid at 50 atm pressure. The total free acid concentration is thus 1% × 0.2 = 0.2% free acid.

At this end of the membrane permeator system we see that the free acid concentration is low and that the permeate will be rather weak in acid.

Cases D, E, F and G are for various ammonium lactate solutions acidified under 50 atmospheres pressure of carbon dioxide gas.

Case D shows 1% ammonium lactate solution. It is seen that of the total acid species, 0.048 fraction are predicted to be acidified.

Case F shows a 10% ammonium lactate solution. 0.015 fraction are predicted to be acidified. This gives a 0.148% concentration of lactic acid to permeate.

Case G shows the weak end of the acid permeation system, we see that for a 1% ammonium lactate and 9% ammonium carbonate feed, that 0.015 fraction of the lactate species are acidified. This gives a 0.015% concentration of lactic acid to permeate.

Clearly acetate (Cases A-C) is more readily acidified than lactate (Cases D-G).

| atm P | [H+] | pH | So | Frac free acid | Wt % free acid |
|---|---|---|---|---|---|
| Case A 1% acetate solution ||||||
| 1 | 1.2825E-6 | 5.89 | .17 | .07 | .07% |
| 10 | 4.3765E-6 | 5.36 | .17 | .20 | .20% |
| 30 | 8.2180E-6 | 5.09 | .17 | .32 | .32% |
| 50 | 1.1209E-5 | 4.95 | .17 | .39 | .39% |
| 100 | 1.7500E-5 | 4.76 | .17 | .50 | .50% |
| Case B 10% acetate solution ||||||
| 1 | 3.9650E-7 | 6.40 | 1.66 | .02 | .22% |
| 10 | 1.2850E-6 | 5.89 | 1.66 | .07 | .68% |
| 30 | 2.2830E-6 | 5.64 | 1.66 | .12 | 1.15% |
| 50 | 3.0000E-6 | 5.52 | 1.66 | .15 | 1.46% |
| 100 | 4.3850E-6 | 5.36 | 1.66 | .20 | 2.00% |
| Case C 1% sodium acetate solution + 9% sodium bicarbonate ||||||
| 1 | 3.9650E-7 | 6.40 | .17 | .02 | .02% |
| 10 | 1.2850E-6 | 5.89 | .17 | .07 | .07% |
| 30 | 2.2830E-6 | 5.64 | .17 | .12 | .12% |
| 50 | 3.0000E-6 | 5.52 | .17 | .15 | .15% |
| 100 | 4.3850E-6 | 5.36 | .17 | .20 | .20% |
| Case D 1% lactate solution ||||||
| 50 | 3.7616E-5 | 4.42 | .110 | 0.048 | 0.048% |
| Case E 1.52% lactate solution ||||||
| 50 | 3.035F-5 | 4.52 | 0.16 g | 0.039 | 0.060% |
| Case F 10% lactate solution ||||||
| 50 | 1.1152E-5 | 4.95 | 1.11 | 0.015 | 0.148% |
| Case G 1% ammonium lactate solution + 9% sodium bicarbonate ||||||
| 50 | 1.1152E-5 | 4.95 | .11 | 0.015 | 0.015% |

Cases A, B, and C show the clear advantage of going to higher pressures in terms of degree of acidification. Higher pressures entail greater costs of compression, recompression, and result in larger volumes of carbon dioxide dissolved in the feed, permeate and retentate streams.

Counterflow and separation factors

Here we find that with balanced flows and makeups, with typical membrane rejections, we can indeed achieve separation. This is somewhat unexpected due to the relatively low extent of acidification acheivable using pressured carbon dioxide.

Example 1: Permeator conversion

Here we simulate a countercurrent flow system with a membrane similiar to a Permasep B-9 synthetic membrane or a cellulose acetate membrane. Both these membranes have been avaialable since the early 1970's. Both these membranes show reasonable rejection of organic acids at pH > 5 and significant permeation at pH < 5.

To predict the inventions performance we need to combine data from some different sources —
1. $CO_2$ membrane permeation data
2. membrane performance data for inorgnaic salts such as $NaHCO3$
3. membrane performance data for salts of organic acids
4. membrane performance data for free acid form organic acids
5. effect of pressurized $CO_2$ on membrane performance
6. effect of pressurized $CO_2$ on acidification of salt solutions of organic acids.

We chose to lump thermodynamic non-idealities into our model.

The real membrane performance data that we base the following simulations on is taken from literature data given in the Background section.

The $CO_2$ acidification data are taken from calculations performed. They are confirmed in examples in a patent regarding liquid extraction using pressurized $CO_2$.

One way the system can be illustrated is as shown in FIG. 1. We simulate this countercurrent system by dividing the length of the membrane system into a series of small steps. In practice, there may be a series of physical membrane units with interstage pumps to overcome pressure drop in the sucessive membrane units. This depends on the permeation rate through the membrane relative to the required flowrate across the membrane required to achieve membrane performance.

Regardless of the actual required length of the membrane system, we can simulate it's performance using our stepwise analysis. This analysis is for a simultaneous reaction and membrane permeation. In this regard, the invention is a carbon dioxide membrane equilibrium reactor used to achieve a simultaneous acidification reaction and separation. This is uniquely different from previous applications of membranes in biochemical separations.

Due to the simultaneous reaction and separation, we cannot readily use a graphical solution to predict separation system performance.

We feed to the mixer sufficient carbon dioxide to saturate the feed mixture plus additional or excess carbon dioxide for reaction. The reaction in the mixer is

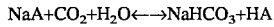

$$NaA+CO_2+H_2O \leftarrow \rightarrow NaHCO_3+HA \qquad \text{Equation 1}$$

Additional species such as $H_2CO_3$, $Na_2CO_3$, $CO_2(g)$, $CO_2(l)$ are also present in equilibrium quantities, but for the purposes of this discussion, do not affect the overall mass balance picture.

At a pressure of 200 psig, we assume 30% of the moles of NaA in the 1 molar feed solution is converted to HA. From this we calculate an equilibrium constant for the above equation 1.

This mixture is then fed to "stage 1" of the permeator. This is a length of membrane sufficient that 90% of the free acid species permeate. In addition, it is assumed that for every 1 mole of acid that permeates, 20 moles of water permeates. This is equivalent to saying that the average concentration of the material travelling through the membrane is $$\frac{1 \text{ mole acid} * 60 \text{ g/mol}}{20 \text{ mol water} * 18 \text{ g/mol} + 1 * 60} * 100\% = 14\% \text{ w/w}$$

This requires that the membrane preferentially permeate the free organic acid species relative to the water species, while rejecting the salt form of the organic acid. While this type of membrane is conceivable, it is not readily available at present.

This example then shows that under these conditions, the invention could work given a suitable membrane.

The product from the $CO_2$ injection mixer is:

| | |
|---|---|
| NaA | 0.70 mole/liter |
| $NaHCO_3$ | 0.30 mole/liter |
| HA | 0.30 mole/liter |
| equilibrium stream after $CO_2$ equilibration calculation | |

STEP 1 simulation: Here, as throughout the membrane reactor-permeator, several events occur simultaneously
 a acidification reaction with excess carbon dioxide
 b. free acid permeation
 c. salt form of acid rejection
 d. bicarbonate and carbonate salt rejection
 e. cation rejection
 f. water permeation
 g. carbon dioxide permeation or back permeation
It is expendient to approximate the actual system behaviour in a stepwise manner. At each step or stage, we calculate event b through g, first and then event a.

Following this case, in stage 1 of the membrane system, we see that the retentate becomes significantly depleted in HA and slightly depleted in water (which is in vast molar excess), while NaA and $NaHCO_3$ are largely retained. This is the mixture identified as "retentate". It is a non-equilibrium mixture. The mixture is

| | |
|---|---|
| NaA | 0.78 mole/liter |
| $NaHCO_3$ | 0.33 mole/liter |
| HA | 0.033 mole/liter |
| non-equilibrium stream after acid permeation calculation | |

Now we simulate the acid base reaction of the excess $CO_2$ present with the NaL, and generate the stream labelled "1", acid base equil. This stream is

| | |
|---|---|
| NaA | 0.64 mole/liter |
| $NaHCO_3$ | 0.47 mole/liter |
| HA | 0.173 mole/liter |
| equilibrium reaction stream after acid base reaction | |

In this stream, for every 100 moles of total acetate species, we find that 21.4 moles are free acid and acetate 78.6 moles are salt form of the acid. This is 21.4% of A-species present at FIA.

We now simulate "stage 2", which physically represents a length of membrane further away from the feed point than stage 1. Here again we permeate free acid through the membrane with copermeated water, and reject $NaHCO_3$ and NaA. The retentate stream, calculated by mass balance, is then equilibrated for the acid-base equilibrium reaction.

Here we see that after permeation and equilibration in the second stage, we now have 17.6% of the total acetate left as free acid. Due to the buildup of increasing levels of bicarbonate, the percentage of free acid available for permeation becomes less and less as we proceed down the permeator. After 2 stages we have removed 41% of the total moles of original acetate species from the feed into the permeate. This can be determined as follows Original mixture: 1.0 moles of NaA Current retentate after stage 2:

0.49 moles of NaA 0.10 moles of HA 0.51 moles of $NaHCO_3$

Acetate removed = 1.0 moles — (0.49 + 0.10) = 0.41 moles

Proceeding to stage 16, we see that we remove 88% of the original acetate by this method after 16 stages.

Example 2: Permeator conversion

Here we follow the case of example 1, but with the following changes

|  | EXAMPLE 1 | EXAMPLE 2 |
|---|---|---|
| STAGEWISE PERFORMANCE CRITERIA |  |  |
| % of free acid mass permeated per stage | 90% | 40% |
| water passage | 20 moles water per 1 mole free acid i.e. some water rejection | [acid] perm = 75% [acid] ret i.e. reflects available membrane performance |
| MAKE UP WATER | NOT NEEDED |  |
| stage 2 |  | 0.18 L/LITER FEED |
| stage 3 |  | 0.21 L/LITER FEED |
| stage 4 |  | 0.21 L/LITER FEED |
| stage 5 |  | 0.21 L/LITER FEED |
| stage 6 |  | 0.21 L/LITER FEED |
| TOTAL |  | 1.02 liter/liter |
| $CO_2$ PRESSURE, |  |  |
| feed side | 200 PSIG | 200 PSIG |
| permeate side | 200 PSIG | 200 PSIG |
| FEED CONCENTRATION |  |  |
| NaA | 1.0 mole/liter | 1.0 mole/liter |
| CALCULATED PERFORMANCE - RESULTS |  |  |
| TOTAL PERMEATE VOLUME, 6 STAGES LITER | 0.24 LITER | 1.62 |
| AVERAGE ACID CONCENTRATION IN SAID PERMEATE mole/liter | 2.8 mole/liter | 0.21 |
| % ACID MASS RECOVERED | 67% | 34% |
| RETENTATE $NaHCO_3$ conc mole/liter | 0.93 mole/liter | 1.02 |
| RETENTATE VOLUME | 0.76 liter | 0.40 liter |

Here we see under more realistic conditions, that a much lower extent of acid recovery has been achieved in 6 stages in example 2. This means that for example 2 conditions, a much larger membrane system will be required to achieve high levels of recovery. Alternatively, the retentate from example 2 could be recycled to the fermentor or other acid generation source to increase acid levels.

Note that in all the examples, "stages" refers to theoretical calculation stages, rather than physical membrane stages. The actual separation can be achieved in one or more membrane modules, depending on the length of the membranes.

Example 3 "Casestudy 6"

Here we refine the calculation technique and use a different basis to calculate permeated water rates. Instead of moles per mole acid permeated used in the earlier calculations, we use assume that of the total liquor present a certain percentage permeates in a given length of membrane or theoretical stage.

We add a small flow of makeup water to each theoretical stage. In practice, this water could be added to each actual pass in a membrane module.

We consider the case of recovery of acetic acid from sodium acetate. The membrane is a theoretical modified cellulose acetate membrane. Membrane rejection parameters are somewhat better than those reported in the literature. We have assumed that by testing a variety of membranes, we can find a membrane slightly better those reported to date.

This calculation thus shows the full potential of this invention. If a membrane is used which has poorer rejection parameters, then more stages or a sequential approach will be needed. This simply would entail feeding the effluent from the simplest form of the invention to an identical second process step. We illustrate this approach in example 6.

CASESTUDY 6

Makeup starts on step: 4
Makeup volume: .10 liter per calculational stage
Membrane length such that: 5.00% of the total liquid permeates
Rejection of NaA salt: 95.00% relative to feed concentration
Rejection of HA free acid: 5.00% relative to feed concentration Temp = 35 deg C.  K'eq = .2667

| | NaA mol | NaHCO3 mol | HA mol | CO2 psig | NaA mol/L | NaHCO3 mol/L | HA mol/L | Volume Liter | % of A- as free A | % of A rmvd |
|---|---|---|---|---|---|---|---|---|---|---|
| STEP 0 | .6000 | .4000 | .4000 | 450 | .60 | .40 | .40 | 1.000 | 40% | 0% |
| STEP 1 | | | | | | | | | | |
| FROM N-1 | .60 | .40 | .40 | | .60 | .40 | .40 | 1.00 | 797 | |
| Permeate | .002 | 0 | .019 | | .03 | 0 | .38 | .05 | | |
| Retentate | .599 | .400 | .381 | | .63 | .42 | .40 | .95 | | |
| Ret + Make | .599 | .400 | .381 | | .630 | .42 | .40 | .95 | | |
| CO2 rxn | .599 | .399 | .380 | | .631 | .420 | .400 | .95 | 39% | 2% |
| STEP 50 | | | | | | | | | | |
| FROM N-1 | .21 | .74 | .15 | | .11 | .39 | .08 | 1.89 | | |
| Permeate | .001 | 0 | .007 | | .01 | 0 | .07 | .09 | | |
| Retentate | .213 | .740 | .139 | | .12 | .41 | .08 | 1.80 | | |
| Ret + Make | .213 | .740 | .139 | | .12 | .41 | .08 | 1.80 | | |
| CO2 rxn | .214 | .739 | .138 | | .119 | .411 | .077 | 1.80 | 39% | 65% |

| TOTALS | NaA mol | NaHCO3 mol | HA mol | NaA mol/L | NaHCO3 mol/L | HA mol/L | liter | Osm.Pres RTCi |
|---|---|---|---|---|---|---|---|---|
| PERMEATE | .0472 | .0000 | .6007 | .0124 | .0000 | .1580 | 3.803 | 68.5 psi |
| RETENTATE | .2135 | .7392 | .1385 | .1188 | .4113 | .0770 | 1.797 | 377.7 psi |

% of acetic acid removed: 64.8%
Ratio of Free Acid to Total in Permeate: 92.71%
wt % Na in retentate: 1.22%
wt % total acetate in retentate: 0.46%
Volume of retentate: 1.80 liter
Free Acid to Total in Retentate: 39.34%

CASESTUDY 11

No makeup
Membrane length such that: 5.00% of the total liquid permeates
Rejection of NaA salt: 95.00% relative to feed concentration
Rejection of HA free acid: 5.00% relative to feed concentration Temp = 35 deg C.  K'eq = .2667

| | NaA mol | NaHCO3 mol | HA mol | CO2 psig | NaA mol/L | NaHCO3 mol/L | HA mol/L | Volume Liter | % of A- as free A | % of A rmvd |
|---|---|---|---|---|---|---|---|---|---|---|
| STEP 0 | .0800 | 0 | .7100 | 450 | .02 | 0 | .15 | 4.700 | 90% | 0% |
| STEP 1 | | | | | | | | | | |
| FROM N-1 | .08 | .00 | .71 | | .02 | 0 | .15 | 4.70 | 61 | |
| Permeate | .000 | 0 | .034 | | .00 | 0 | .14 | .24 | | |
| Retentate | .080 | 0 | .676 | | .02 | 0 | .15 | 4.47 | | |
| Ret + Make | .080 | 0 | .676 | | .018 | 0 | .15 | 4.47 | | |
| CO2 rxn | .030 | .050 | .726 | | .007 | .011 | .163 | 4.47 | 964 | 4% |
| STEP 50 | | | | | | | | | | |
| FROM N-1 | .03 | .05 | .07 | | .08 | .12 | .18 | .38 | | |
| Permeate | .000 | 0 | .003 | | .00 | 0 | .17 | .02 | | |
| Retentate | .031 | .045 | .065 | | .08 | .13 | .18 | .36 | | |
| Ret + Make | .031 | .045 | .065 | | .08 | .13 | .18 | .36 | | |
| CO2 rxn | .03, | .045 | .065 | | .085 | .125 | .181 | .36 | 68% | 88% |

| TOTALS | NaA mol | NaHCO3 mol | HA mol | NaA mol/L | NaHCO3 mol/L | HA mol/L | liter | Osm.Pres RTCi |
|---|---|---|---|---|---|---|---|---|
| PERMEATE | .0039 | .0000 | .6901 | .0009 | .0000 | .1591 | 4.338 | 60.3 psi |
| RETENTATE | .0307 | .0454 | .0653 | .0849 | .1254 | .1806 | .362 | 199.7 psi |

%of acetic acid removed: 87.8%
Ratio of Free Acid to Total in Permeate: 99.43%
wt % Na in retentate: .4837%
wt % total acetate in retentate: 1.09%
Volume of retentate: .36 liter
Free Acid to Total in Retentate: 68.02%

Example 5, Casestudy 12

This is an example of concentrating the effluent from Casestudy 11 using a commercially available reverse osmosis membrane. No applied carbon dioxide pressure or backpressure or reaction occurs or is needed for this concentrating step. No acidification is achieved. Simply, the product acetic acid is retained and water is permeated, permitting a concentration of the dilute acetic acid stream.

line 26 to the fermenter 16 to control the pH. Backpressure in line 23 is controlled by valve 27.

This 4.7 litre/hour of permeate from system 1 is pumped from 450 psig to 1200 psig and fed via line 28 to a second membrane acidification — purification system 29. Additional carbon dioxide may be added via line 30 at 450 psig. This system has sufficient membrane area — flow path length such that a separation equivalent to the 50 calculational stages of Casestudy 11 is achieved. A backpressure of

| CASESTUDY 12 |||||||||||
| --- | --- | --- | --- | --- | --- | --- | --- | --- | --- | --- |
| No Makeup ||||||||||
| Membrane length such that ||| | 5.00% of the total liquid permeates ||||||
| Rejection of NaA salt ||| | 99.50% relative to feed concentration ||||||
| Rejection of HA free acid ||| | 98.50% relative to feed concentration ||||||
| | NaA mol | NaHCO3 mol | HA mol | CO2 psig | NaA mol/L | NaHCO3 mol/L | HA mol/L | Volume Liter | % of A- as free A | % of A rmvd |
| | | Temp = 35 deg C. || | | K'eq = .2667 || | | |
| STEP 0 | .0039 | 0 | .6901 | 450 | .00 | 0 | .16 | 4.34 | 99% | 0% |
| STEP 1 | | | | | | | | | | |
| FROM N-1 | .00 | .00 | .69 | | .00 | 0 | .16 | 4.34 | 53 | |
| Permeate | .000 | 0 | .001 | | .00 | 0 | .00 | .22 | | |
| Retentate | .004 | 0 | .690 | | .00 | 0 | .17 | 4.12 | | |
| Ret + Make | .004 | 0 | .690 | | .001 | 0 | .17 | 4.12 | | |
| CO2 rxn | .002 | .002 | .692 | | .000 | .001 | .168 | 4.12 | 100% | 0% |
| STEP 50 | | | | | | | | | | |
| FROM N-1 | .00 | .00 | .67 | | .01 | .00 | 1.89 | .35 | | |
| Permeate | .000 | 0 | .000 | | .00 | 0 | .03 | .02 | | |
| Retentate | .003 | .000 | .665 | | .01 | .00 | 1.99 | .33 | | |
| Ret + Make | .003 | .000 | .665 | | .01 | .00 | 1.99 | .33 | | |
| CO2 rxn | .003 | .000 | .665 | | .010 | .001 | 1.993 | .33 | 99% | 4% |
| TOTALS | NaA mol | NaHCO3 mol | HA mol | | NaA mol/L | NaHCO3 mol/L | HA mol/L | liter | Osm.Pres RTCi ||
| PERMEATE | .0000 | .0000 | .0255 | | .0000 | .0000 | .0064 | 4.004 | 2.4 psi ||
| RETENTATE | .0034 | .0005 | .6651 | | .0102 | .0014 | 1.9926 | .334 | 669.5 psi ||

| | |
| --- | --- |
| % of acetic acid removed | 3.7% |
| Ratio of Free Acid to Total in Permeate | 99.87% |
| wt % Na in retentate | .0266% |
| wt % total acetate in retentate | 11.95% |
| Volume of retentate | .33 liter |
| Free Acid to Total in Retentate | 99.49% |

Example 6

"Casestudies 6, 11 combined with Casestudy 12, with recycles"

Figure 2:
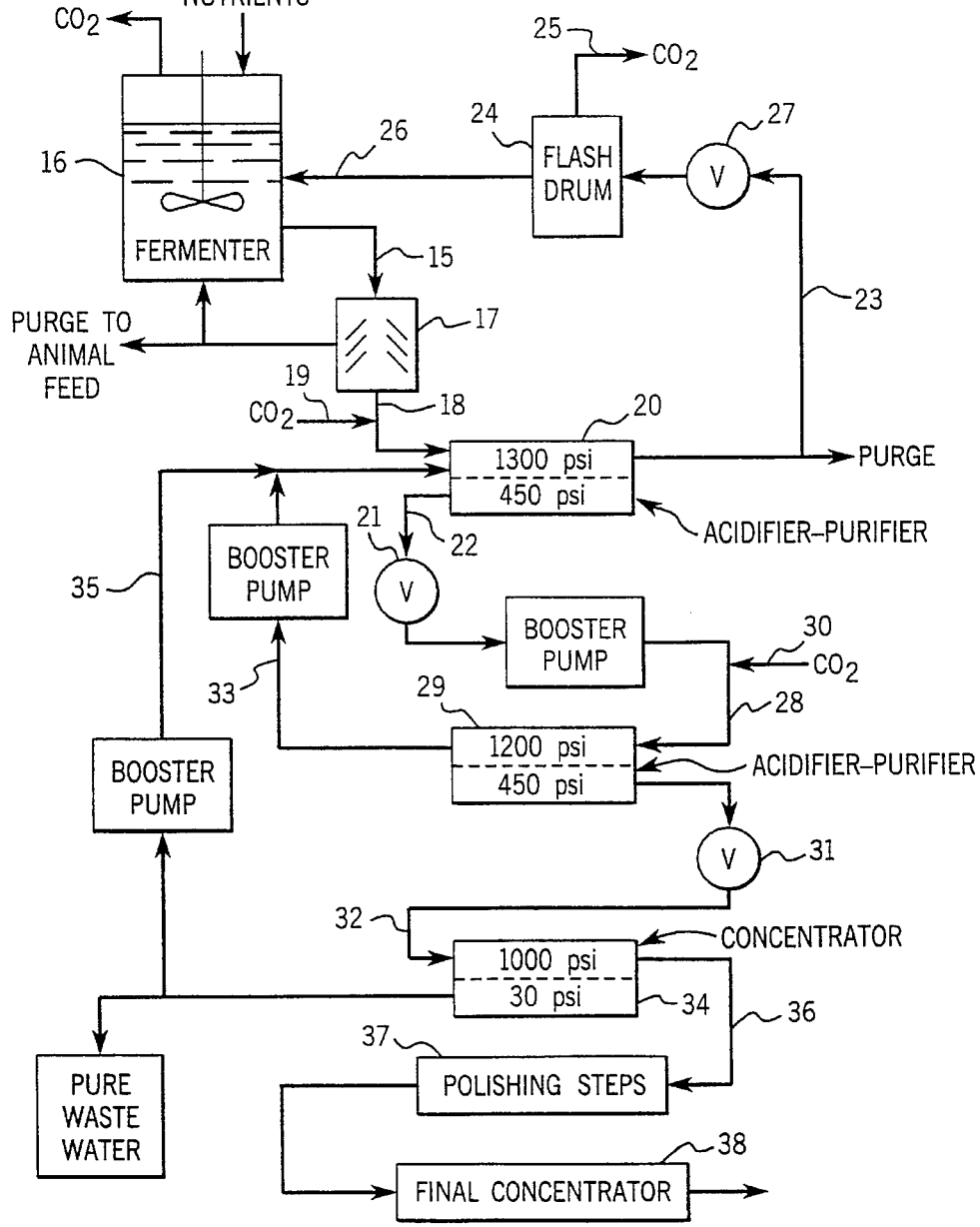
FIG. 2 is a schematic diagram of a multi-stage process for recovering lactic acid from an aqueous crude fermentation broth containing sodium lactate in accordance with the present invention.

We illustrate this in FIG. 2.

A crude broth in line 15 containing 1 mol/liter of sodium acetate, cells and other impurities from a fermentor 16 is pretreated in a clarifier 17 by centrifugation, ultrafiltration, micrfofiltration, precipitation, or other means to give a partially purified solution in line 18.

This solution in line 18, containing 1 mol/liter of sodium acetate, is mixed with pressurized carbon dioxide in line 19 at 450 psig and 35 degree celcius and fed to the first membrane acidification — purification system 20. This membrane system 20 has membrane area and flow path length such that a separation equivalent to the 50 calculational stages of Casestudy 6 is achieved. A backpressure of 450 psig is maintained via valve 21 on the permeate side. A total of 4.6 litre of makeup water or very dilute sodium acetate is added to the feed side. From this stage, a permeate of 4.7 liter/hour of material containing 79% of the total acetate species present in the feed is recovered in line 22. Of this permeated acetate, 92.7% is free acid and 7.3% is sodium acetate. The retentate in line 23 passes to a pressure release drum 24, carbon dioxide is recovered via line 25, and the liquor, rich in sodium bicarbonate, can be recycled via 450 psig is maintained on the permeate side by valve 31. No makeup water is added to the feed side. From this stage, a permeate of 4.34 liter/hour is collected via line 32. This permeate contains 69% of the acetate species present in the system 1 feed. Of this permeated acetate, 99.43% is free acid and 0.37% is sodium acetate. The retentate from system 2 can be recycled via line 33 to system 1.

The permeate from system 2 passes to a concentrating membrane 34, as illustrated in casestudy 12. This concentrator 34 could also be a freeze concentrator, an evaporator, or other concentrating device. The permeate or water recovered, 4.00 liter/hour can be returned via line 35 to system 1 as part of the makeup water added. The concentrate or retentate in line 36 is 11% acetic acid and has greater than 99% purity. This acetic acid can then be passed to finishing polishing purification steps 37 and final concentrating steps 38 if desired.

I claim:

1. A process for the recovery of an organic acid from an aqueous solution that is rich in salts of said organic acid, comprising:

mixing a crude broth containing a mixture of organic acids and salts of organic acids with pressurized $CO_2$;

applying pressure to the mixture of crude broth and pressurized $CO_2$ so that the mixture may be fed to a membrane having a retentate side and a permeate side;

applying backpressure on the permeate side of said membrane;

passing said mixture over said membrane while under said pressure with the membrane being of a type that largely rejects the salt form of organic acids, but largely permeates the acid form, while maintaining backpressure on the membrane permeate side equal to or greater than the pressure applied to said mixture, to form a retentate stream and a permeate stream;

and collecting permeated liquor from the permeate stream.

2. The process of claim 1 wherein the membrane used is composed of a material selected from: cellulose acetate; cellulose acetate-cellulose triacetate blend; polyamide/polysulfone; polyvinyl alcohol; sulfonated polysulfone; sulfonated polyethersulfone; polyethylenimine crosslinked with m-tolylene-2,4-diisocyanate; a ceramic.

3. The processes of claim 1 further including the step of reducing pressure on the retentate stream so that carbon dioxide is released.

4. The process of claim 1 wherein the broth contains lactic acid and lactate salts of at least 95% optically purity and the permeate is at 95% optically pure.

5. The process of claim 1 wherein the aqueous solution has a pH in the range 3.0 to 9.0.

6. The process of claim 1 wherein the pressure of carbon dioxide is in the range from atmospheric pressure up to 2500 psig.

7. The process of claim 1 wherein makeup water is added to the retentate side to enhance the separation.

8. The process of claim 1 wherein the permeate is withdrawn countercurrently from the membrane system relative to the retentate flow.

9. The process of claim 1 wherein the organic acid is selected from acetic, formic, pyruvic, lactic, hydroxyacetic, propionic, citric, acyrlic, beta-hydroxybutyric, oxalic, citraconic, malic, maleic, succinic acid or a mixture of said acids, and the base of the salt is selected from calcium, potassium, ammonium, magnesium, or sodium.

10. The process of claim 1 wherein the broth is selected from a crude or partially purified broth derived from fermentation of sugars to produce a lactic acid and salts of lactic acid; a crude or partially purified broth derived from the digestion of lactic acid polymers; ethanol distillation bottoms containing acids; citrus processing waste streams; pineapple processing wastes; spent sulfite liquor waste water; wood processing waste streams containing acids.

11. The process of claim 1 wherein the retentate stream is recycled back to a fermentation or other process requiring pH control.

12. The process of claim 1 wherein the broth is pre-treated to remove materials that might foul the membranes.

13. The process of claim 1 wherein an organic solvent other than water is used on the permeate side to help retain the acid on the permeate side of the system.

14. The process of claim 1 wherein the permeated liquor is fed to at least one additional membrane of the type that rejects the salt form but permeates the acid form.

15. The process of claim 1 wherein the permeated liquor is concentrated further using a reverse osmosis membrane system.

16. A process for the recovery of an amino acid from an aqueous solution that is rich in salts of said amino acid comprising:

mixing a crude broth containing a mixture of amino acids and salts of amino acids with pressurized $CO_2$;

applying pressure to the mixture of crude broth and pressurized $CO_2$ so that the mixture may be fed to a membrane having a retentate side and a permeate side;

passing said mixture over said membrane while under said pressure with the membrane being of a type that largely rejects the anion form of organic acids, but largely permeates the cation form, while maintaining backpressure on the membrane permeate side equal to or greater than the pressure applied to said mixture to form a retentate stream and a permeate stream; and collecting permeated liquor from the permeate stream.

* * * * *

UNITED STATES PATENT AND TRADEMARK OFFICE
CERTIFICATE OF CORRECTION

PATENT NO. : 5,522,995
DATED : June 4, 1996
INVENTOR(S) : Michael C.M. Cockrem

It is certified that error appears in the above-indentified patent and that said Letters Patent is hereby corrected as shown below:

IN THE CLAIMS:

Claim 16, Col. 18, Line 30 (Claim 18, Line 8,

Add the following paragraph between Lines 8 and 9:
---applying backpressure on the permeate side of said membrane---.

Signed and Sealed this

Thirty-first Day of December, 1996

Attest:

BRUCE LEHMAN

*Attesting Officer*    Commissioner of Patents and Trademarks